United States Patent [19]

Göpferich

[11] Patent Number: 6,086,908
[45] Date of Patent: Jul. 11, 2000

[54] IMPLANTS WITH PHASED RELEASE OF MEDICAMENTS

[75] Inventor: Achim Göpferich, Sinzing, Germany

[73] Assignee: Achim Goepferich, Germany

[21] Appl. No.: 09/142,227
[22] PCT Filed: Feb. 20, 1997
[86] PCT No.: PCT/EP97/00820
§ 371 Date: Jul. 15, 1999
§ 102(e) Date: Jul. 15, 1999
[87] PCT Pub. No.: WO97/32570
PCT Pub. Date: Sep. 12, 1997

[30] Foreign Application Priority Data

Mar. 5, 1996 [DE] Germany .......................... 196 08 423

[51] Int. Cl.⁷ .................................................. A61F 2/00
[52] U.S. Cl. .......................... 424/424; 424/425; 424/426
[58] Field of Search .................................. 424/424, 425, 424/426

[56] References Cited

U.S. PATENT DOCUMENTS 4,450,150  5/1984  Sidman .

FOREIGN PATENT DOCUMENTS 111144      6/1984   European Pat. Off. .
2424169    12/1974   Germany .
2424169A   12/1974   Germany .
92/02211    2/1992   WIPO .

*Primary Examiner*—Carlos A. Azpuru
*Attorney, Agent, or Firm*—Millen, White, Zelano & Branigan, P.C.

[57] ABSTRACT

The invention relates to implants with phasewise release of pharmaceutical substance, which consist of a core and layers arranged concentrically around it. The core and at least one of the layers contain different pharmaceutical substances or the same pharmaceutical substance in different doses. The pharmaceutical substance-containing areas consist of surface-eroding biodegradable polymer materials.

5 Claims, 2 Drawing Sheets

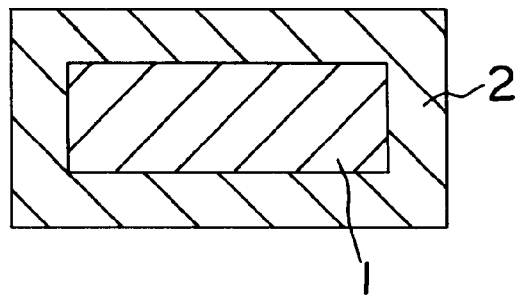
F I G. 1
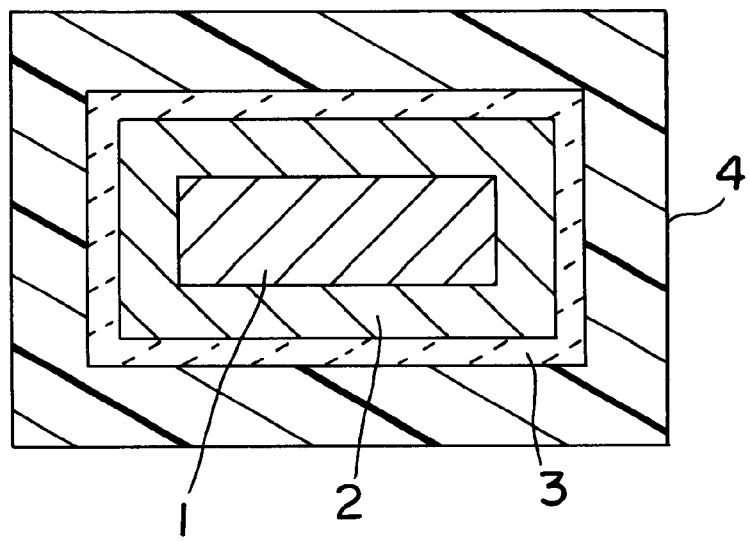
F I G. 2

IMPLANTS WITH PHASED RELEASE OF MEDICAMENTS

This application is a Rule 371 continuation of PCT International Application PCT/EP97/00820, filed on Feb. 20, 1997, which is a continuation of German Application 196 08 423.7, filed on Mar. 5, 1996.

The invention relates to novel implants for the release of pharmaceutical substance. These allow the same pharmaceutical substance to be released in two or more phases or two or more pharmaceutical substances to be released in a chronologically predetermined sequence. The implants consist of layers of biodegradable polymers which erode completely within a few weeks in the body.

Research in the field of controlled release of pharmaceutical substance originally concentrated on releasing pharmaceutical substances at a constant rate in order to achieve constant plasma or tissue levels. However, it was recognized that the discontinuous release of pharmaceutical substances can also be very advantageous. By this means, for example, the development of tolerances can be prevented and in immunization higher immune responses can be achieved. A further field of application for pharmaceutical forms having discontinuous release is tumour therapy. Tumour cells tend to develop resistances if the same active compound is administered continuously. Implants which release pharmaceutical substances discontinuously or sequentially could counteract this development. An example of the potential use of such implants is the treatment of tumours in the area of the central nervous system. It is therefore desirable to have available locally implantable pharmaceutical release systems which make possible a phasewise release of different pharmaceutical substances or the same pharmaceutical substance at different concentrations.

It has now been found that implants having a multilayer structure of pharmaceutical substance-containing layers allow a phasewise release of pharmaceutical substance if the pharmaceutical substance-containing areas of these implants consist of surface-eroding biodegradable polymer materials.

The invention thus relates to implants with phasewise release of pharmaceutical substance, which consist of a core and layers arranged concentrically around it, the core and at least one of the layers comprising different pharmaceutical substances or the same pharmaceutical substance in different doses, which are characterized in that the pharmaceutical substance-containing areas of the implants consist of surface-eroding biodegradable polymer materials.

The implants according to the invention consist of a core and one or more layers of surface-eroding biodegradable polymer materials arranged around it concentrically, which can have different erosion rates.

BRIEF DESCRIPTION OF THE DRAWINGS

FIG. 1 shows the schematic structure of a two-layer implant in cross-section. The core 1 is surrounded by a coating layer 2. Core 1 and coating layer 2 consist of surface-eroding biodegradable polymer materials and contain the respective pharmaceutical substance.

FIG. 2 shows the schematic structure of a four-layer implant in cross-section. Here, a core 1 is surrounded by two intermediate layers 2 and 3. A jacket layer 4 is arranged around them. Core 1 and jacket layer 4 consist of surface-eroding biodegradable polymer materials and contain the respective pharmaceutical substance. The intermediate layers 2 and 3 likewise consist of biodegradable polymer materials and are free of pharmaceutical substance.

Figure 3:
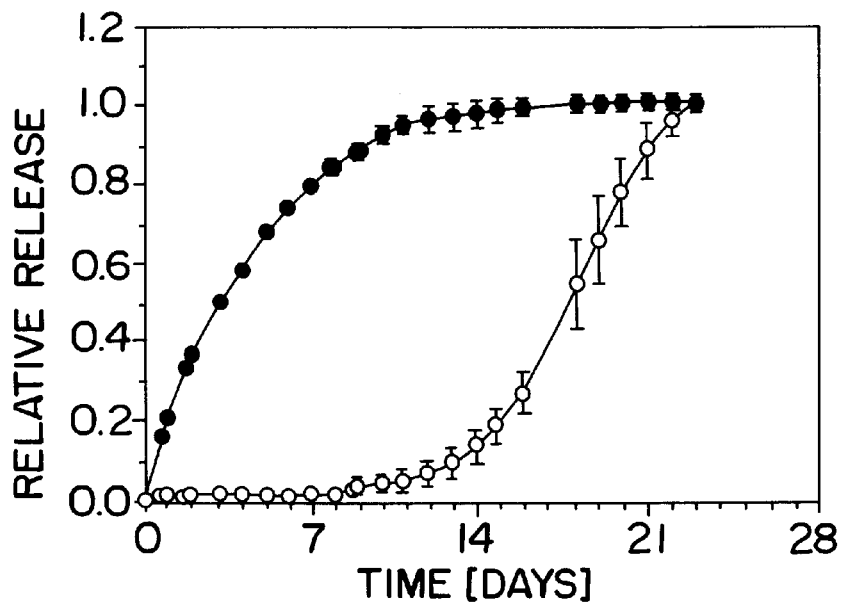
FIG. 3 shows the release from implants, in which first Carboxyfluorescein and then Brilliant Blue are released.

In the simplest embodiment according to FIG. 1, the implant consists of a pharmaceutical substance-containing core and a pharmaceutical substance-containing coating layer. By appropriate choice of the polymer materials, whose biodegradability in the body is surface erosion-controlled, it is guaranteed that the respective pharmaceutical substance is released phasewise exclusively from the surface corresponding to the degradation of the polymer material. The chronological duration and the release profile can be controlled by selection of the polymer materials according to differing degradability. Depending on the dimensioning of the coating layer and core and also the dose of the pharmaceutical substances embedded therein, their release can in each case take place strictly separately for days or weeks.

The pharmaceutical substance-containing areas of the implant can be loaded with different pharmaceutical substances. This is useful if a combination therapy with chronological graduation is demanded. The pharmaceutical substance-containing areas of the implant, however, can also contain one and the same pharmaceutical substance in different doses. By this means, optimum therapy is possible by means of chronologically graduated, differing doses of pharmaceutical substance.

In a preferred embodiment, for example as shown in FIG. 2, between the pharmaceutical substance-containing areas 1 and 4 of the implant are arranged pharmaceutical substance-free intermediate layers 2 and 3. The latter likewise consist of biodegradable polymer materials. Preferably, these consist of bulk-eroding degradable polymer materials which are only slowly degraded. By this means, an even stricter separation of the pharmaceutical substance release from the various pharmaceutical substance-loaded areas of the implant can be effected.

The most diverse biodegradable polymer materials and their degradation properties are known to the person skilled in the art. A selection according to surface-eroding or bulk-eroding degradability is possible without problems, if appropriate by using simple tests as a guide.

Compared with monolithic implants, the implants according to the invention are distinguished by a greater flexibility in release. This makes possible the use of the implants in immunization and can prevent development of tolerance in local tumour therapy.

The discontinuous release of a pharmaceutical substance and the sequential release of two or more pharmaceutical substances, as is often used, for example, in systemic chemotherapy is thus also possible in therapy using implants.

In spite of the higher complexing ability of the implants, these can be prepared using simple processes which allow mass production, such as, for example, compression, coating or extrusion. No disadvantages thus result with respect to preparation.

The preparation of implants according to the invention can be carried out, for example, as follows:

I. The polymers are first loaded with pharmaceutical substances for the preparation of the pharmaceutical substance-carrying layers (layer 1 and 2 or 1 and 4) shown in FIGS. 1 and 2. Two methods are suitable for this.

The corresponding polymers are fused and the pharmaceutical substances are dissolved or suspended in the melt. After solidification, the solid pharmaceutical substance-loaded polymer is obtained. This method is suitable, for example, for all heat-stable pharmaceutical substances.

The polymers are dissolved in an organic solvent. The pharmaceutical substance is dissolved or suspended in this mixture. By evaporating the solvent, a solid polymer/pharmaceutical substance mixture is obtained.

II. In a second step, the pharmaceutical substance-containing polymers are ground to give a flowable powder for the preparation of rapidly eroding layers (layer 1, 2 in FIG. 1 or 1 and 4 in FIG. 2).

III. The core 1 of the implant (see FIGS. 1 and 2) is prepared by compressing the pharmaceutical substance-containing polymer powder. A hydraulic press or a tablet press, for example, is suitable for this purpose.

IV. The preparation of a two-layer implant (see FIG. 1) is carried out like the preparation of laminated tablets.

V. The pharmaceutical substance-free intermediate layers 2 and 3 for multilayer implants (see FIG. 2) are prepared by compressing pharmaceutical substance-free polymer granules. To do this, for example, a base disc is first pre-pressed, on which is centered the core 1. An appropriate amount of polymer granules is heaped over it and then compressed. The application of the third layer can also be carried out by repeated immersion in a 20% polymer solution. The material used is a bulk-eroding polymer. The article is then dried for 48 hours. Finally, pressing-on of a pharmaceutical substance-loaded jacket 4 is carried out analogously to step IV.

The following examples show the release profile of low molecular weight substances from a four-layer implant. The model substances used are Brilliant Blue and Carboxyfluorescein. Investigation of the release was carried out at 37° C. in 10 ml of 0.1 M of phosphate buffer solution, pH 7.4. The content determination was carried out photometrically.

Instead of these model substances, any desired pharmaceutical substances can be employed for the release investigations.

EXAMPLE 1

Implants with sequential release of two different low-molecular weight substances:
Materials Used:

| Layer | Polymer | Colourant | Loading (%) |
|---|---|---|---|
| Core 1 | p(CCP-SA)20:8* | Brilliant Blue | 30 |
| Layer 2 | p(CPP-SA)20:8* | — | — |
| Layer 3 | poly(D,L-lactide) | — | — |
| Layer 4 | p(CPP-SA)20:8* | Carboxyfluorescein | 5 |

*poly[1,3 bis (p-carboxyphenoxy)propane-co-sebacic acid].20:80 [sic]

Geometric Dimensions and Weight:

| Implant | Height [mm] | ø [mm] | Weight [mg] |
|---|---|---|---|
| Core 1 | 0.95 ± 0.05 | 4 | 14.0 ± 0.5 |
| Layer 2 | 1.74 ± 0.03 | 6 | 56.4 ± 1.1 |
| Layer 3 | 1.90 ± 0.07 | n.d.** | 64.8 ± 1.5 |
| Layer 4 | 3.52 ± 0.04 | 8 | 202.2 ± 2.3 |

**not determined

FIG. 3 shows the release from implants, in which first Carboxyfluorescein and then Brilliant Blue are released. The release of Brilliant Blue during the first 10 days is largely suppressed and only commences to an increased extent after this time.

EXAMPLE 2

Implants with sequential release of the same substance

Materials Used:

| Layer | Polymer | Colourant | Loading (%) |
|---|---|---|---|
| Core 1 | p(CCP-SA)20:8* | Brilliant Blue | 60 |
| Layer 2 | p(CPP-SA)20:8* | — | — |
| Layer 3 | poly(D,L-lactide) | — | — |
| Layer 4 | p(CPP-SA)20:8* | Brilliant Blue | 5 |

*poly[1,3 bis(p-carboxyphenoxy)propane-co-sebacic acid].20:80 [sic]

Geometric Dimensions and Weight:

| Implant | Height [mm] | ø [mm] | Weight [mg] |
|---|---|---|---|
| Core 1 | 0.89 ± 0.03 | 4 | 14.6 ± 0.5 |
| Layer 2 | 2.55 ± 0.06 | 6 | 89.4 ± 2.8 |
| Layer 3 | 2.92 ± 0.07 | n.d.** | 103.9 ± 3.9 |
| Layer 4 | 4.50 ± 0.09 | 8 | 268.4 ± 2.9 |

**not determined

Figure 4:
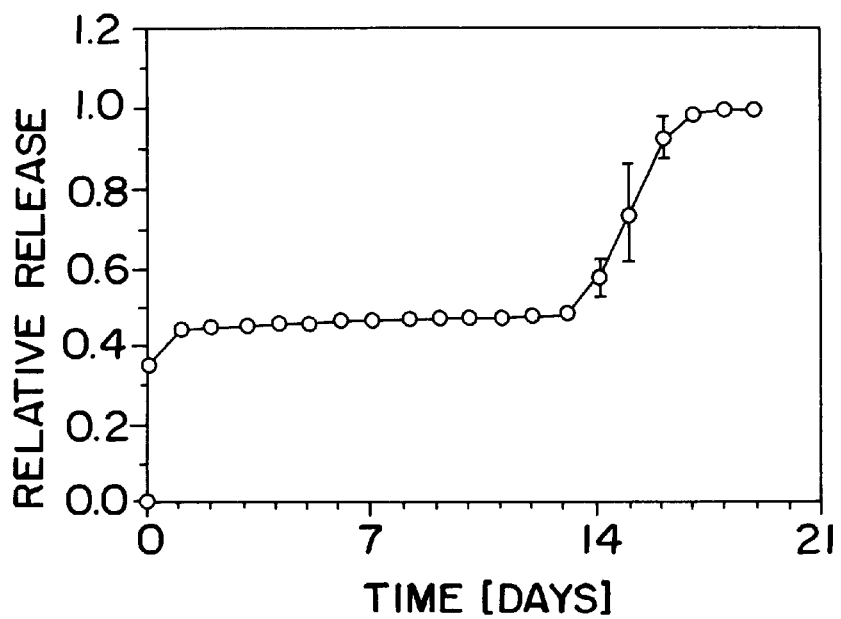
FIG. 4 shows the release of Brilliant blue from implants having a core 1 and layers 2, 3, and 4 as shown in Example 2.

FIG. 4 shows the release of Brilliant Blue from such systems. In the first and second phases, in each case 50% Brilliant Blue is released.

What is claimed is:

1. An implant for phase-wise release of pharmaceutical agents, comprising:

a core and a plurality of layers arranged concentrically around said core, wherein the core and at least one of said layers comprise different pharmaceutical agents, or the same pharmaceutical agent in difference doses, wherein the pharmaceutical-comprising areas of the implant comprise a surface-eroding biodegradable polymer, and wherein there is at least one pharmaceutical agent-free layer comprising a biodegradable polymer between at least two said layers comprising a pharmaceutical agent.

2. An implant of claim 1, wherein the core and at least one layer comprise different pharmaceutical agents.

3. An implant of claim 1, wherein the core and at least one layer comprise different doses of the same pharmaceutical agent.

4. An implant of claim 1, wherein the pharmaceutical agent-free layer comprises a bulk-eroding polymer.

5. An implant of claim 1, wherein there are two pharmaceutical agent-free layers comprising a biodegradable polymer between two said layers comprising a pharmaceutical agent.

* * * * *